United States Patent
Mercati

(10) Patent No.: US 6,207,189 B1
(45) Date of Patent: Mar. 27, 2001

(54) PROCEDURE FOR THE PRODUCTION OF CAPSULES AND TABLETS OF NATURAL SUBSTANCES OF VEGETABLE ORIGIN

(75) Inventor: Valentino Mercati, Cittá di Castello—Perugia (IT)

(73) Assignee: Aboca di Mercati Valentino & C. Societa Semplice, Arezzo (IT)

( * ) Notice: Subject to any disclaimer, the term of this patent is extended or adjusted under 35 U.S.C. 154(b) by 0 days.

(21) Appl. No.: 09/468,341

(22) Filed: Dec. 21, 1999

(30) Foreign Application Priority Data

Aug. 10, 1999 (EP) .................................................. 99830519

(51) Int. Cl.$^7$ .............................. A61K 9/20; A61K 9/48; A61K 9/14; A61K 9/16
(52) U.S. Cl. ......................... 424/464; 424/451; 424/489; 424/490
(58) Field of Search .................................... 424/439, 451, 424/464, 250, 361, 489, 490

(56) References Cited

U.S. PATENT DOCUMENTS 3,622,677 * 11/1971 Short ..................................... 424/361
4,384,005 * 5/1983 McSweeney .......................... 426/250

FOREIGN PATENT DOCUMENTS

| 3712058 | 10/1988 | (DE) . |
| 0457075 | 11/1991 | (EP) . |
| 0800860 | 10/1997 | (EP) . |
| 2285117 | 4/1976 | (FR) . |

OTHER PUBLICATIONS

Encyclopedia Brittanica (Acessed Mar. 3, 2000) www.search.eb.com/bol/topic?eu.*

* cited by examiner

Primary Examiner—Jon P. Weber
Assistant Examiner—Patricia Patten
(74) Attorney, Agent, or Firm—Dennison, Scheiner, Schultz & Wakeman

(57) ABSTRACT

A procedure for the production of tablets and capsules of natural substances of vegetable origin, in which dry extracts and micronized powders of one or more medicinal herbs are mixed in appropriate proportions. The mixture is then subjected to granulation by means of steam at atmospheric pressure, dry air is introduced for the elimination of the steam and to start the drying process, through which the granules produced by the steam are consolidated, before they are put into the machine that will make the tablets and capsules, without the use of excipient or adjuvant substances.

6 Claims, 1 Drawing Sheet

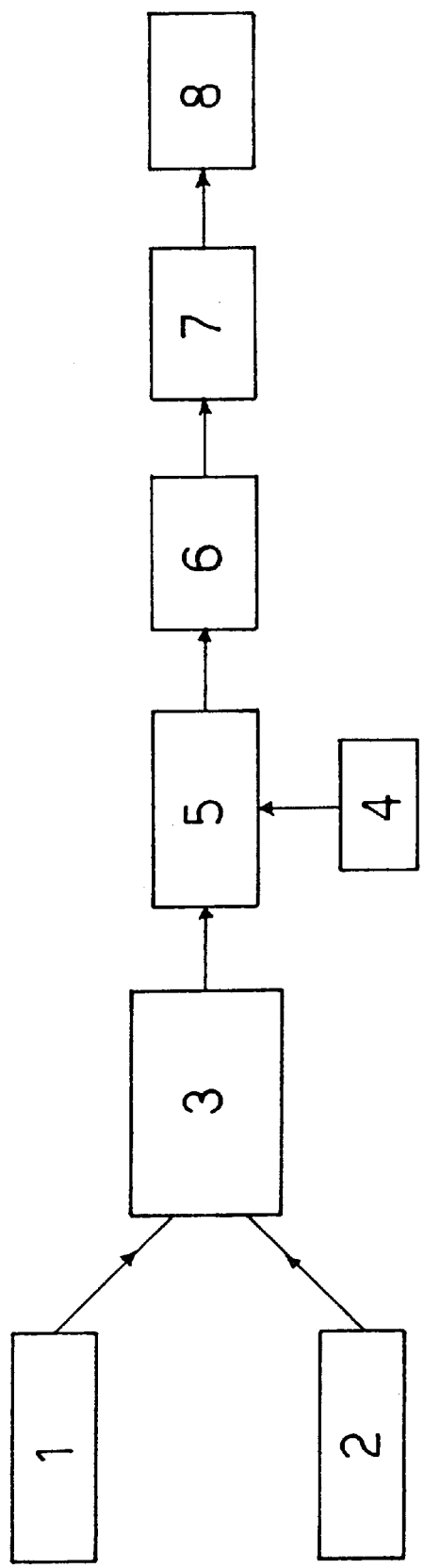

PROCEDURE FOR THE PRODUCTION OF CAPSULES AND TABLETS OF NATURAL SUBSTANCES OF VEGETABLE ORIGIN

BACKGROUND OF THE INVENTION

1. Field of the Invention

The invention concerns a procedure for the production of tablets and capsules of natural substances of vegetable origin, without the use of technologic excipients or adjuvants, in the field of herbal medicine and pharmaceutical products.

2. Description of Related Art

At present it is possible to produce tablets, containing natural substances of vegetable origin, through the compression of a mixture of dry extracts and/or herbal powders with the addition of a number of excipients, also called technologic adjuvants. The latter are normally synthetic or semi-synthetic substances and, according to their functions, they are divided into:

binders: their function is to tie the powder particles together to obtain the tablet;

lubricants: their function is to reduce the adhesion of the powders to the machines and, in particular, to the matrix and punch with which the tablets are produced, as well as to increase the flowability of the mixture of powders during the compression phase.

Therefore, the tablets and capsules obtained through the known technologies normally contain 30%–60% of their weight in excipients that must be used only and exclusively for technological reasons. Therefore it is impossible to produce, at the state of the art, 100% natural tablets which contain only dry extracts and/or herbal powders.

On the other hand it could be theoretically possible to eliminate the need of technologic adjuvants by prior granulation of the mixture to be pressed. The hypothetically produced granulate could in fact lose its characteristics of low flowability and binding power or excessive adhesiveness and it could be correctly pressed.

But, even with the state of the art machines and methods for granulation (wet, dry, fluid bed), it is not possible to granulate without the use of excipients and more specifically of binding agents.

This invention rises from the observation that dry extracts and herbal powders, but in particular their mixtures, usually possess good binding properties, but have very little flowability. It would therefore be possible to produce tablets and/or capsules simply by modifying this last characteristic, that is by increasing the flowability of the mixture. Using the granulation process, the flowability of mixture is considerably improved, but to obtain granules this process requires the use of binding agents or the use of liquids (water or solvents) which, after having caused the aggregation of particles into granules, must be evaporated and therefore taken away from the granule.

The latter solution would be the only one possible to obtain a granulate and therefore a tablet or a capsule without excipients, but in this specific case, since the dry extracts are extremely hygroscopic, due to their low humidity content (<5%), it is technically impossible to have a wet granulation of the product.

SUMMARY OF THE INVENTION

The aim of the present invention is to overcome the obstacles that exist in the present state of the art, and to identify a procedure to make the production of tablets and capsules possible without using technologic excipients and adjuvants. This will allow the production of tablets and capsules that are 100% natural and contain only 100% of dry extract and/or herbal powders, single or mixed together in the ratio required for the effect expected after their ingestion. In this way, we can reduce at least the number or weight of the tablets or capsules that must be ingested to obtain, for example, a specific pharmacological effect.

The procedure, which has made these results possible, is embodied in the mixing of the dry extracts and of the micronized powders, of one or more medicinal herbs, blended in the appropriate ratio. Then the mixture undergoes a granulation process with the aid of steam at atmospheric pressure, for a time interval of some fractions of a second, followed by the introduction of dry air, in the first place to eliminate the steam and in the second to effect a drying process with which to consolidate the granules that are produced, before they are introduced into the machine that forms the tablets and capsules, without the use of technological excipients or adjuvants.

The said procedure is particularly effective since it gives rise to granules that are extremely flowing and with the adhesive characteristic that do not require the addition of technologic excipients neither in the granulation step nor in the compression one. The substantial novelty, in respect to the other known techniques, is represented by the fact that the procedure uses steam at atmospheric pressure as moisting agent which, after its contact with the powders to generate the granulation, is quickly removed by dry air, immediately after humidifying section where the granules are formed, in a section in which the product is dried after having reached the granule stage.

BRIEF DESCRIPTION OF THE DRAWING

The documentation of the invention contains the block diagram, which shows, schematically, a flow chart exemplifying structure and steps of the apparatus and process that constitute the invention.

In the block diagram, which appears in the enclosed FIGURE, is indicated:

with 1 the tank containing dry extracts of an herb or a mixture of them;

with 2 the tank containing micronized powders of an herb or a mixture of them;

with 3 the tank in which dry extracts and micronized powders are mixed together in the appropriate ratio;

with 4 the atmospheric pressure steam generator;

with 5 the chamber or station in which the two components coming from chamber 3 are made to interact with the atmospheric pressure steam originating in generator 4;

with 6 the station furnished with the drying group in which steam is eliminated by a flow of dry air and humidified mixture in the shape of granules is dried;

with 7 the chamber in which the mixture is accumulated, in the form of dry granules;

with 8 the machine or plant in which the granules are transformed into tablets, capsules or other forms appropriate for ingestion.

DESCRIPTION OF THE PREFERRED EMBODIMENT(S)

In general, the procedure in object contemplates the use of one or more natural vegetable products, mixed together in the required proportions so as to obtain, in the finished product, the desired proportion of active agents.

Said product or mixture of products, previously cleaned, selected, cut etc., is transformed, in part into a dry extract and in the other part into micronized powders. The first are fed into tank 1 the second into tank 2. The contents of tanks 1 and 2 are mixed in the appropriate proportions in tank 3 so that they are in the correct condition for transformation into granules.

The granulation effect, obtained in chamber 5 is the basis of the innovation, which has brought about the results of the present invention. This derives from the technical observation that the dry extracts and micronized powders of vegetable origin being used, are constituted by hydrophilic and lipophilic substances that are not distributed uniformly inside the individual powder particles of the mixture contained in tank 3. When the latter (the powder particles), inside the granulation chamber 5, are hit by the atmospheric pressure steam current originating from the generator 4, the hydrophilic substances dissolve immediately and the resulting solution is distributed evenly inside and on the surface of the powder particles. We have, at the level of each particle, a sort of suspension of lipophilic substances in a water medium, made up presumably of a solution of mono and polysaccharides contained in the dry extract of herbs and/or in the micronized powder of herbs. These hydrophilic substances, once the water evaporates in the drying chamber or station 6, crystallise uniformly inside and on the surface of each particle. The result obtained in each particle is the formation of a granule which, due to the elimination of the water and the final drying process in the chamber 6, presents a surface that is 2–3 times larger, per unit of weight, than the non granulated product. This gives rise to a considerable reduction in the specific weight. It has also been found that the crystallisation of the hydrophilic substances in the granule reduces the hygroscopic capacity of the product and this characteristic remains even if the granules are ground very finely. This means that dissolving-crystallisation process has not only taken place on the surface but also inside each particle of powder.

The dry granulated product stored in the chamber 7, before it is transformed into tablets, capsules or other, due to the regular shape of the granules and the decrease in the hygroscopic capacity, compared to the dry extract of herbs, presents a very high flowability, much higher than that of the dry extract of herbs and of the micronized herbal powders, making it suitable for pressing or encapsulating in total absence of technologic excipients.

In all of the granulation step and in the following ones starting from chamber 3 up to chamber 7 and up to machine 8, it is absolutely unnecessary to use binders which are instead required, even in this type of product, by the conventional known granulation methods.

The water (as steam)/product contact time inside the granulator 5 is extremely short, fractions of second, but it is sufficient to obtain, inside chamber 7, a dry granulate that is unaltered and has not lost, due to the phenomena of hydrolysis or thermal degradation, the active components contained in the herbal dry extracts and powders.

The dry granulate, in the production of tablets, is carried to the pressing machine which presses it directly, without the aid of technologic excipients and adjuvants.

The dry granulate, in the production of capsules, is carried to the filling machine, in which the capsules are filled without using excipients or technologic agents.

The invention is shown in its use with reference to a practical application for the production of tablets.

Example: Tablets of a natural concentrated mixture of Hawthorn, dry extract and powder:

in tank 1 dry extract of Hawthorn;

in tank 2 micronized powder of Hawthorn;

in tank 3 Hawthorn dry extract (50%), Hawthorn micronized powder (50%);

in station 5, the product coming from tank 3 is made to react with steam for second's fractions. While the mixture is falling from a higher to a lower level it is crossed by a laminar flow of steam at atmospheric pressure and a temperature of 50°–70° C.;

the station 6 is constituted by a rotating drum dryer in which dry air, at a temperature of 40° C., is introduced. It has a rotation speed of about 10 rad/min. and the product exits on a conveyor belt;

the dry granulate collected in chamber 7 feeds a rotating press where the tablets, each of 450 mg., are produced, without the addition of any excipients therefore by direct compression.

What is claimed is:

1. A process for the preparation of tablets or capsules from a composition consisting essentially of at least one natural vegetable substance in a form selected from the group consisting of dry extracts, micronized powders and mixtures thereof, said composition not containing technological excipients, comprising the steps of:

a) granulating said at least one natural vegetable substance in the presence of steam at atmospheric pressure for a period of less than about one second;

b) introducing dry air to dry the granulated at least one natural vegetable substance;

c) consolidating the dried, granulated at least one natural vegetable substance for preparation of the tablets or capsules; and d) tableting or encapsulating the consolidated, dried and granulated at least one natural vegetable substance.

2. The process of claim 1, wherein the at least one natural vegetable substance comprises a water soluble component and a non-water soluble component, the steam is present for a time sufficient to dissolve the water soluble component, and the dry air causes crystallization of the dissolved water soluble component around the non-water soluble component during the drying.

3. The process of claim 1, wherein the granulated at least one natural vegetable substance is dried in a rotating drum dryer.

4. The process of claim 1, wherein the dried, granulated at least one natural vegetable substance is tabulated or encapsulated in a tableting or capsule filling machine.

5. The process of claim 1, wherein the composition consists of said at least one natural vegetable substance.

6. The process of claim 1, wherein the at least one natural vegetable substance falls through a laminar flow of steam, wherein the steam is at a temperature of 50 to 70° C.

* * * * *